(12) United States Patent
Keusenkothen et al.

(10) Patent No.: US 10,843,981 B2
(45) Date of Patent: *Nov. 24, 2020

(54) CATALYTIC AROMATIZATION

(71) Applicant: ExxonMobil Chemical Patents Inc., Baytown, TX (US)

(72) Inventors: Paul F. Keusenkothen, Houston, TX (US); Samia Ilias, Somerville, NJ (US); John Scott Buchanan, Flemington, NJ (US); Mayank Shekhar, Houston, TX (US); Reyyan Koc-Karabocek, Houston, TX (US); Teng Xu, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/469,725

(22) Filed: Mar. 27, 2017

(65) Prior Publication Data

US 2017/0305812 A1    Oct. 26, 2017

Related U.S. Application Data

(60) Provisional application No. 62/327,023, filed on Apr. 25, 2016.

(30) Foreign Application Priority Data

Jun. 20, 2016  (EP) .................................. 16175164

(51) Int. Cl.
*C07C 2/76* (2006.01)
*B01J 29/06* (2006.01)
(Continued)

(52) U.S. Cl.
CPC ............... *C07C 2/76* (2013.01); *B01J 29/061* (2013.01); *B01J 29/405* (2013.01); *B01J 29/48* (2013.01);
(Continued)

(58) Field of Classification Search
None
See application file for complete search history.

(56) References Cited

U.S. PATENT DOCUMENTS 3,702,886 A    11/1972  Argauer et al.
3,960,978 A     6/1976  Givens et al.
(Continued)

FOREIGN PATENT DOCUMENTS

CN    103100415    6/2015
CN    105618127    6/2016
(Continued)

OTHER PUBLICATIONS

Mravec et al., Synthesis of the zeolite ZSM-5 using seed crystals, Chem. Papers (45), 1991, pp. 27-33. (Year: 1991).*
(Continued)

*Primary Examiner* — Philip Y Louie (57) ABSTRACT

The invention relates to catalytic aromatization, e.g., for the conversion of non-aromatic hydrocarbon to higher-value aromatic hydrocarbon, to catalysts useful for such aromatization, to methods for making such catalysts, and to systems and apparatus for carrying out aromatization in the presence of the catalyst.

30 Claims, 3 Drawing Sheets

Propane Conversion for Catalysts E, M, and N at 550°C, 15 psig (103 kPa), 0.5 hr⁻¹WHSV, 37:19:15:9:20 vol./vol. % of $C_1:C_2:C_3:C_4:Ar$ (51) Int. Cl.
*C01B 39/06* (2006.01)
*B01J 29/48* (2006.01)
*C10G 35/085* (2006.01)
*C10G 35/06* (2006.01)
*B01J 29/40* (2006.01)
*B01J 29/85* (2006.01)
*B01J 37/00* (2006.01)
*B01J 37/28* (2006.01)
*B01J 27/22* (2006.01)

(52) U.S. Cl.
CPC .............. *B01J 29/85* (2013.01); *C01B 39/06* (2013.01); *C10G 35/065* (2013.01); *C10G 35/085* (2013.01); *B01J 27/22* (2013.01); *B01J 37/0009* (2013.01); *B01J 37/28* (2013.01); *B01J 2229/18* (2013.01); *C07C 2529/40* (2013.01); *C07C 2529/85* (2013.01); *Y02P 20/52* (2015.11)

(56) References Cited

U.S. PATENT DOCUMENTS

| | | | |
|---|---|---|---|
| 4,021,502 A | 5/1977 | Plank et al. | |
| 4,080,395 A | 3/1978 | Butter | |
| 4,150,062 A | 4/1979 | Garwood et al. | |
| 4,157,293 A * | 6/1979 | Plank | B01J 29/40 208/135 |
| 4,227,992 A | 10/1980 | Garwood et al. | |
| 4,456,781 A | 6/1984 | Marsh et al. | |
| 5,510,016 A * | 4/1996 | Hilbert | C10G 35/095 208/89 |
| 5,919,722 A | 7/1999 | Verduijn et al. | |
| 5,936,135 A * | 8/1999 | Choudhary | C07C 2/00 585/407 |
| 5,998,686 A | 12/1999 | Clem et al. | |
| 6,074,975 A | 6/2000 | Yao et al. | |
| 7,659,437 B2 | 2/2010 | Iaccino et al. | |
| 7,759,535 B2 | 7/2010 | Iaccino et al. | |
| 7,772,447 B2 | 8/2010 | Iaccino et al. | |
| 8,835,706 B2 | 9/2014 | Iyer et al. | |
| 8,841,227 B2 | 9/2014 | Sangar et al. | |
| 8,981,169 B2 | 3/2015 | Iaccino et al. | |
| 2008/0027254 A1 | 1/2008 | Zhou et al. | |
| 2009/0209794 A1 | 8/2009 | Lauritzen et al. | |
| 2011/0054232 A1 * | 3/2011 | Sangar | B01J 29/076 585/417 |
| 2011/0124933 A1 * | 5/2011 | Kiesslich | B01J 29/48 585/417 |
| 2011/0257452 A1 | 10/2011 | Khabashesku et al. | |
| 2011/0270002 A1 | 11/2011 | Yanagawa et al. | |
| 2015/0174561 A1 * | 6/2015 | McCarthy | B01J 29/90 585/408 |
| 2015/0174570 A1 * | 6/2015 | Loveless | B01J 29/061 585/408 |

FOREIGN PATENT DOCUMENTS

| | | |
|---|---|---|
| WO | 2010/140005 A2 | 12/2010 |
| WO | 2010140005 A9 | 12/2010 |
| WO | 2017/052856 | 3/2017 |

OTHER PUBLICATIONS

Huayun Long et al. "Effect of lanthanum and phosphorous on the aromatization activity of Zn/ZsM-5 in FCC gasoline upgrading", Microporous and Mesoporous Materials, vol. 198, Jul. 19, 2014, pp. 29-34.
Aritani, H. et al., J. of Environmental Sciences "Methane dehydroaromatization over Mo-modified H-MFI for gas to liquid catalysts", vol. 6, pp. 736-ff, 2009.
Chen, Nal Y. et al., Ind. Eng.Chem. Process Des. Dev., 1986, 25, 151-155.
Liu, Y. et al., ACS Catal. 2016, 6, 5366-5370.
Lermer, H. et al., "Synthesis and structure refinement of ZSM-5 single crystals", Zeolites, 1985, vol. 5, May p. 131.
Tabak, S.A. et al., "Production of Synthetic Gasoline and Diesel Fuel From Non-Petroleum Resources", p. 293-299, 1986 https://web.anl.gov/PCS/acsfuel/preprint%20archive/Files/31_2_NEW%20YORK_04-86_0293.pdf.
Liu, Y. et al., (Supporting Information), "Efficient Conversion of Methane to Aromatics by Coupling Methylation Reaction", ACS Catal., 2016, 6 (8), pp. 5366-5370.
Zhou, Ming et al., Synthesis of Mesoporoous ZSM-5 Zeolite Crystals by Conventional Hydrothermal Treatment, Electronic Supplementary Material (ESI) for RSC Advances, royal Society of Chemistry 2013.
Xu et al., "Performance of a binder-free, spherical-shaped Mo/HZSM-5 catalyst in the non-oxidative CH4dehydroaromatization in fixed- and fluidized-bed reactors under periodic CH4-H2switch opera," chemical Engineering and Processing, 2013, vol. 72, pp. 90-102.

* cited by examiner

Figure 1

C$_{6+}$ Yield for Catalysts A, B, C and D at 550°C, 15 psig (103 kPa), 1 hr$^{-1}$ WHSV, 46:24:19:11 vol./vol.% of C$_1$:C$_2$:C$_3$:C$_4$

Figure 2

C$_{6+}$ Yield for Catalysts E, F and G at 550°C, 15 psig (103 kPa), 1 hr$^{-1}$ WHSV, 46:24:19:11 vol./vol.% of C$_1$:C$_2$:C$_3$:C$_4$

Figure 3

$C_{6+}$ Yield for Catalysts H, I and J at 550°C, 15 psig (103 kPa),
1 $hr^{-1}$ WHSV, 46:24:19:11 vol./vol.% of $C_1:C_2:C_3:C_4$

Figure 4

$C_{6+}$ Yield for Catalysts K and L at 550°C, 15 psig (103 kPa),
1 $hr^{-1}$ WHSV, 46:24:19:11 vol./vol.% of $C_1:C_2:C_3:C_4$

Figure 5

Propane Conversion for Catalysts E, M, and N at 550°C, 15 psig (103 kPa), 0.5 hr$^{-1}$WHSV, 37:19:15:9:20 vol./vol. % of $C_1:C_2:C_3:C_4$:Ar

CATALYTIC AROMATIZATION

PRIORITY

This application claims priority to and the benefit of U.S. Provisional Application No. 62/327,023, filed Apr. 25, 2016, and EP Application No. 16175164.9, filed Jun. 20, 2016, the disclosures of which are incorporated herein by reference in their entireties.

FIELD OF THE INVENTION

The invention relates to catalytic aromatization, e.g., for the conversion of non-aromatic hydrocarbon to higher-value aromatic hydrocarbon, to catalysts useful for such aromatization, to methods for making such catalysts, and to systems and apparatus for carrying out aromatization in the presence of the catalyst.

BACKGROUND OF THE INVENTION

With the shale gas revolution, natural gas supply has become less expensive and more abundant, making it an advantageous feedstock to upgrade. One difficulty encountered in direct and indirect natural gas upgrading processes is the lack of sufficient infrastructure in many locations for economical transport of the gas to distant conversion facilities. This has led to the development of processes for converting light paraffinic hydrocarbon in the natural gas to an aromatic-rich naphtha, which can be further upgraded to gasoline and other valuable products such as benzene, toluene, and xylenes (collectively, "BTX").

Conventional light paraffin aromatization processes can be carried out directly or indirectly. For example, direct conversion processes such as Cyclar (available from UOP) and M2 Forming (available from ExxonMobil) typically convert $C_{2+}$ light paraffinic hydrocarbon to aromatic hydrocarbon using a conventional moving-bed catalyst. Indirect processes, on the other hand, include separating the methane from the natural gas, and then converting the methane to syngas. The syngas is then converted to liquid hydrocarbon.

One difficulty encountered in indirect aromatization processes results from the inefficiencies that arise from the need for the methane separation and upgrading facilities. A difficulty encountered in direct processes results from the refractory nature of the methane and ethane in the natural gas, which make these compounds more difficult to convert using convenient temperature, pressure, and flow conditions. Another difficulty, which is encountered in direct and indirect processes, results from a significant decrease in aromatic hydrocarbon yield that occurs during the course of the aromatization. The yield decrease typically results from an accumulation of deposits (e.g., catalyst coke and coke precursors) in the aromatization reactor, and particularly proximate to the catalyst. Frequent catalyst regeneration is needed to maintain appreciable aromatic hydrocarbon yield.

Therefore, a need exists for aromatization processes which can be operated long-term with appreciable conversion and appreciable yield of aromatic hydrocarbon and with decreased selectivity to catalyst coke compared to conventional processes. In particular, hydrocarbon conversion catalysts are desired which are more resistant to coking and which can operate in long-term and with less need for regeneration as compared to conventional catalysts, especially catalysts which can be used in fixed-bed processes. The instant invention meets this need and others.

SUMMARY OF THE INVENTION

The invention is based in part on the discovery of catalytically active materials (e.g., catalysts) that are more resistance to deactivation during aromatization than are conventional aromatization catalysts. The catalysts are suitable for use in fixed beds, and can be operated in aromatization (e.g., dehydrocyclization) service for substantially longer time intervals without regeneration or rejuvenation than is the case with conventional aromatization catalysts.

Accordingly, certain aspects of the invention relate to a process for producing aromatic hydrocarbon from a feedstock comprising non-aromatic hydrocarbon in at least one reaction zone which contains at least one catalyst having catalytic activity to form aromatic hydrocarbon from the feedstock's non-aromatic hydrocarbon. The catalyst comprises at least one molecular sieve component and at least one dehydrogenation component. The molecular sieve component is present in the catalyst in an amount ≥80 wt. % based on the weight of the catalyst, and (iv) the dehydrogenation component comprises at least one element from Groups 3 to 15 of the Periodic Chart. At least a portion of the feedstock's aromatic hydrocarbon is converted to aromatic hydrocarbon to produce a product comprising ≥1 wt. % of the aromatic hydrocarbon. The conversion is carried out in the reaction zone in the presence of the catalyst under conversion conditions, which include a temperature ≥400° C.

In other aspects, the invention relates to a catalytically active material comprising: ≤5 wt. % of at least one active metal and ≥80 wt. % of at least one molecular sieve. The molecular sieve has a framework of interconnected atoms, an outer surface, and a plurality of pores having an average pore size of 4 Å to 7 Å. The active metal is selected from Groups 3 to 13 of the Periodic Chart. At least 90 wt. % of the active metal is located in the pores, and ≤10 wt. % of the active metal is proximate to the outer surface. The catalytically active material includes ≤10 wt. % of metal in any form other than (A) framework metal, if any, and (B) the active metal. The catalytically active material contains ≤20 wt. % of binder.

In other aspects, the invention relates to making a catalytically active material. The catalytically active material includes molecular sieve produced from a synthesis mixture. The synthesis mixture comprises at least one aluminum source, water, a templating agent, and one silica source. At least 90 wt. % of the silica source comprises $SiO_2$ impregnated with at least one metal, or compound thereof, selected from Groups 3 to 13 of the Periodic Chart. The aluminum source, the water, the templating agent, and other components of the synthesis mixture if any together comprise ≤0.1 wt. % of silicon. The synthesis mixture is reacted under hydrothermal reaction conditions to produce a reaction product comprising a molecular sieve. At least a portion of the molecular sieve is formed into a solid body containing ≤20 wt. % of binder based on the weight of the solid body. At least a portion of the molecular sieve is activated before or after formation of the solid body to produce the catalytically active material.

BRIEF DESCRIPTION OF THE DRAWINGS

FIG. 5 illustrates the time dependence of propane conversion at 550° C., 15 psig (103 kPa), 0.5 WHSV. The propane is present in a model light paraffinic hydrocarbon feedstock which comprises 37 vol./vol. % of methane, 19 vol./vol. % of ethane, 15 vol./vol. % of the propane, 9 vol./vol. % of C$_4$ alkane, and 20 Vol./Vol. % Ar. The feedstock is contacted with Catalysts E, M, and N to form the naphtha, which comprises C$_{6+}$ hydrocarbon.

DETAILED DESCRIPTION OF THE INVENTION

The process of this invention for dehydrocyclization of non-aromatic hydrocarbon such a light (C$_2$-C$_5$) paraffinic hydrocarbon, e.g., to produce aromatic hydrocarbon. The dehydrocyclization is carried out in the presence of at least one active material having catalytic activity for hydrocarbon dehydrocyclization. The active material includes a molecular sieve component and a dehydrogenation component. The molecular sieve component comprises ≥80 wt. % of the active material, e.g., ≥90 wt. %, such as ≥95 wt. %, or ≥99 wt. %. Typically, ≥50 wt. % of the remainder of the active material comprises the dehydrogenation component, e.g., ≥75 wt. %, such as ≥90 wt. %, or ≥95 wt. %. The dehydrogenation includes at least one metal selected from Groups 3 to 15 of the Periodic Chart, typically from Groups 5 to 15 of the Periodic Chart. Optionally, the dehydrogenation component includes a second metal. The first and second metals are referred to herein as "active" metals to distinguish them from metal that may be present in the molecular sieve component such as framework aluminum present in a molecular sieve framework. It has been found that such active materials, which include little or no binder (e.g., matrix), exhibit increased time-on-stream and lower reduction in yield of aromatic hydrocarbon with increased time-on-steam as compared to metal-containing molecular sieve-based catalysts which contain a greater amount of binder. The invention will be further described with reference to the following definitions.

Definitions

For the purpose of this specification and appended claims, the following terms are defined.

The term "time-on-stream" means the time in which the catalyst is in contact with the feedstock under the specified catalytic hydrocarbon conversion conditions, e.g., under aromatization conditions, such as dehydrocyclization conditions.

The term "C$_n$" hydrocarbon means a hydrocarbon having n carbon atom(s) per molecule, wherein n is a positive integer. The term "C$_{n+}$" hydrocarbon means a hydrocarbon having at least n carbon atom(s) per molecule. The term "C$_{n-}$" hydrocarbon means a hydrocarbon having no more than n carbon atom(s) per molecule. The term "hydrocarbon" or "hydrocarbons" means a class of compounds containing a hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The terms "alkane" and "paraffinic hydrocarbon" mean substantially-saturated compounds which substantially contain hydrogen and carbon only, e.g., those containing ≤1% (molar basis) of unsaturated carbon atoms. As an example, the term alkane encompasses C$_2$ to C$_{20}$ linear, iso, and cyclo-alkanes.

The terms "unsaturated" and "unsaturated hydrocarbon" refer to one or more C$_{2+}$ hydrocarbon compounds which contain at least one carbon atom directly bound to another carbon atom by a double or triple bond.

The terms "aromatics" and "aromatic hydrocarbon" mean a class of hydrocarbon compounds containing at least one aromatic ring.

The terms "non-aromatic" and "non-aromatic hydrocarbon" mean a class of hydrocarbon compounds comprising ≤1 wt. % of carbon atoms included in aromatic rings.

The term "naphtha" means a mixture of aromatic hydrocarbon having six or more carbon atoms, also referred to as a C$_{6+}$ aromatic hydrocarbon, such as, for example, a mixed xylene.

The term "reaction zone" or "reactor zone" mean a location within a reactor, e.g., a specific volume within a reactor, for carrying out a specified reaction. A reactor or reaction stage may encompass one or more reaction zones. More than one reaction may be carried out in a reactor, reactor stage, or reaction zone.

The term "molecular sieve of the MCM-22 family" (or "MCM-22 family material" or "MCM-22 family") includes one or more of:

(i) molecular sieves made from a common first degree crystalline building block unit cell, which unit cell has the MWW framework topology. (A unit cell is a spatial arrangement of atoms which if tiled in a three-dimensional space describes the crystal structure. Such crystal structures are discussed in the "Atlas of Zeolite Framework Types", Fifth edition, 2001, the entire content of which is incorporated as reference.);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and (iv) molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the Cu K-alpha doublet as incident radiation and a diffractometer equipped with a scintillation counter and associated computer as the collection system.

The term "constraint index" is defined in U.S. Pat. Nos. 3,972,832 and 4,016,218, which are incorporated herein by reference.

The term "conversion" when used in connection with a specified reactant in a reaction means the amount (weight basis) of the reactant consumed in the reaction. For example, when the specified reactant is propane ($C_3$ hydrocarbon), 100% conversion means 100% of the propane is consumed in the reaction. Conversion may also be indicative of the activity of a catalyst where a higher activity catalyst has a high conversion, and a low activity catalyst has a lower activity. The term "selectivity" refers to the production (on a weight basis) of a specified compound in a catalytic reaction. As an example, the phrase "a light hydrocarbon conversion reaction has a 100% selectivity for aromatic hydrocarbon" means that 100% of the light hydrocarbon (weight basis) that is converted in the reaction is converted to aromatic hydrocarbon. The term "yield" refers to the production of a specified compound or a class of compounds in a catalytic reaction, and is substantially equal to conversion times selectivity.

The term "weight hourly space velocity", referred to as "WHSV" means the quotient of the mass flow rate of the reactants divided by the mass of the catalyst.

The term "Periodic Chart" means the Periodic Chart of the Elements, as it appears on the inside cover of The Merck Index, Twelfth Edition, Merck & Co., Inc., 1996.

The process for producing aromatic hydrocarbon includes the step of catalytically converting a non-aromatic feedstock, e.g., a light paraffinic hydrocarbon feedstock which comprises non-aromatic hydrocarbon. The catalytic conversion can include not only catalytic aromatization, but also catalytic dehydrocyclization which typically produces aromatic hydrocarbon in addition to cyclic non-aromatic hydrocarbon. As used herein, the term "aromatization" encompasses both catalytic dehydrocyclization and catalytic aromatization. Representative aromatization feedstocks will now be described in more detail. The invention is not limited to these feedstocks, and this description is not meant to foreclose other feedstocks within the broader scope of the invention.

Representative Feedstock

The feedstock typically comprises one or more $C_2$ to $C_9$ non-aromatic hydrocarbon compounds, e.g., one or more light hydrocarbon (i.e., $C_2$ to $C_5$) compounds, such as one or more paraffinic light hydrocarbon compounds. For example, the feedstock can comprise ≥1 wt. % based on the weight of the feedstock of one or more of (i) paraffinic $C_2$ to $C_9$ hydrocarbon, (ii) aliphatic $C_2$ to $C_9$ hydrocarbon, (iii) aliphatic paraffinic $C_2$ to $C_9$ hydrocarbon, (iv) paraffinic light hydrocarbon, (v) aliphatic light hydrocarbon, and (vi) aliphatic paraffinic light hydrocarbon; such as ≥10 wt. %, or ≥25 wt. %, or ≥50 wt. %, or ≥75 wt. %, or ≥90 wt. %, or ≥95 wt. %. Although methane alone is typically too refractory to be aromatized except under the most severe of the specified aromatization conditions, methane in combination with one or more $C_{2+}$ hydrocarbon can be aromatized under less severe conditions of temperature and pressure.

Optionally, the feedstock further comprises diluent. Diluent present in the feedstock's source (e.g., $CO_2$ present in natural gas) and diluent added to the feedstock are within the scope of the invention. Diluent, when present, is typically included in the feedstock in an amount ≤60 wt. % based on the weight of the feedstock, e.g., ≤50 wt. %, such as ≤40 wt. %, or ≤30 wt. %, or ≤20 wt. %, or ≤10 wt. %. A feedstock constituent is diluent when it is substantially non-reactive under the specified reaction conditions in the presence of the specified catalyst, e.g., molecular nitrogen, and nobler gasses such as argon.

The feedstock typically contains $C_3$ and/or $C_4$ hydrocarbon e.g., (i) ≥20 wt. % propane, such as ≥40 wt. %, or ≥60 wt. %, and/or (ii) ≥20 wt. % butanes, such as ≥40 wt. %, or ≥60 wt. %. The amount of $C_{5+}$ hydrocarbon when present is typically small, e.g., ≤20 wt. %, such as ≤10 wt. %, or ≤01 wt. %. Typically, the feedstock contains ≤10 wt. % of $C_{6+}$ saturated hydrocarbon, e.g., ≤5 wt. %.

The feedstock can contain methane, e.g., ≥1 wt. % methane, such as ≥10 wt. %, or ≥20 wt. %, or ≥60 wt. %. Even under process conditions where methane is non-reactive (e.g., methane as diluent) its presence is beneficial, e.g., to decrease total hydrocarbon partial pressure during the conversion, which in turn lessens the amount of coke and coke precursors formed during the conversion. Typically, the feedstock comprises a total of ≤10 wt. % of impurities such as CO, $CO_2$, $H_2S$, and total mercaptan; e.g., ≤1 wt. %, or ≤0.1 wt. %. Optionally, the feedstock comprises molecular hydrogen, e.g., ≥1 wt. % molecular hydrogen based on the weight of the feedstock, such as ≥5 wt. %.

Optionally, the feedstock contains unsaturated $C_{2+}$ hydrocarbon, such as $C_2$-$C_5$ unsaturated hydrocarbon. When present, the amount of $C_{2+}$ unsaturated hydrocarbon is typically ≤20 wt. %, e.g., ≤10 wt. %, such as ≤1 wt. %, or ≤0.1 wt. %, or in the range of from 0.1 wt. % to 10 wt. %. The feedstock can be substantially-free of non-aliphatic hydrocarbon. More particularly, the feedstock can be substantially-free of aromatic hydrocarbon, where substantially-free in this context means ≤1 wt. % based on the weight of the feedstock, such as ≤0.1 wt. %, or ≤0.01 wt. %, or ≤0.001 wt. %. One representative feedstock comprises ≤1 wt. % ethane; ≤1 wt. % of aromatic hydrocarbon; and ≥1 wt. % of $C_{3+}$ paraffinic hydrocarbon, e.g., ≥10 wt. % of a mixture of $C_3$ and $C_4$, such as ≥50 wt. %, or ≥75 wt. %, or in the range of 80 wt. % to 99 wt. %. Another representative feedstock comprises (i) 10 wt. % to 40 wt. % ethane and ≤1 wt. % of aromatic hydrocarbon; with the feedstock further comprising (ii) 1 wt. % to 40 wt. % methane, (iii) 20 wt. % to 50 wt. % propane, and (iv) 20 wt. % to 50 wt. % butanes.

The feedstock's light hydrocarbon can be obtained from one or more sources of hydrocarbon, e.g., from natural hydrocarbon sources including those associated with producing petroleum, or from one or more synthetic hydrocarbons sources such as catalytic and/or non-catalytic reactions. Examples of such reactions include catalytic cracking, catalytic reforming, coking, steam cracking, etc. Synthetic hydrocarbon sources include those in which hydrocarbon within a geological formation has been purposefully subjected to one or more chemical transformations. The feedstock can include recycle components, e.g., methane, molecular hydrogen, and $C_{2+}$ non-aromatic hydrocarbon.

In certain aspects, the source of light hydrocarbon includes natural gas, e.g., raw natural gas ("raw gas"). Natural gas is (i) a mixture comprising hydrocarbon, (ii) primarily in the vapor phase at a temperature of 15° C. and a pressure of 1.013 bar (absolute), and (iii) withdrawn from a geologic formation. Natural gas can be obtained, e.g., from one or more of petroleum deposits, coal deposits, and shale deposits. The natural gas can be obtained by conventional production methods but the invention is not limited thereto. Raw natural gas is a natural gas obtained from a geologic formation without intervening processing, except for (i) treatments to remove impurities such as water and/or any other liquids, mercaptans, hydrogen sulfide, carbon dioxide; and (ii) vapor-liquid separation, e.g., for adjusting the relative amounts of hydrocarbon compounds (particularly the relative amounts of $C_{4+}$ hydrocarbon compounds) in the natural gas; but not including (iii) fractionation with reflux. Conventional methods can be used for removing impurities and/or adjusting the relative amount of hydrocarbon compounds present in the feedstock, but the invention is not limited thereto. One suitable raw natural gas comprises 3 mole % to 70 mole % methane, 10 mole % to 50 mole % ethane, 10 mole % to 40 mole % propane, and 5 mole % to 40 mole % butanes and 1 mole % to 10 mole % of total $C_5$ to $C_9$ hydrocarbon. In certain aspects, ≥50 wt. % of the feedstock comprises natural gas, such as raw natural gas, e.g., ≥75 wt. %, or ≥90 wt. %, or ≥95 wt. %.

Any form of raw gas can be used as a source material, although the raw gas is typically one or more of (i) gas obtained from a natural gas well ("Gas Well", Non-associated", or "Dry" gas), (ii) natural gas obtained from a condensate well ("Condensate Well Gas"), and (iii) casing head gas ("Wet" or "Associated" gas). Table 1 includes typical raw gas compositional ranges (mole %) and, parenthetically, typical average composition (mole %) of certain raw gasses.

TABLE 1

| Component | Associated Gas | Dry Gas | Condensate Well Gas |
|---|---|---|---|
| $CO_2$ | 0-50 (0.63) | 0-25 (0) | 0-25 (0) |
| $N_2$ | 0-50 (3.73) | 0-25 (1.25) | 0-25 (0.53) |
| $H_2S$ | 0-5 (0.57) | 0-5 (0) | 0-5 (0) |
| $CH_4$ | 0-80 (64.48) | 0-97 (91.01) | 0-98 (94.87) |
| $C_2H_6$ | 5-20 (11.98) | 2-10 (4.88) | 1-5 (2.89) |
| $C_3H_8$ | 2-10 (8.75) | 0.5-5 (1.69) | 0.1-5 (0.92) |
| i-butane | 0.1-5 (0.93) | 0.05-1 (0.14) | 0.1-5 (0.31) |
| n-butane | 1-5 (2.91) | 0.05-2 (0.52) | 0.05-2 (0.22) |
| i-pentane | 0.05-2 (0.54) | 0.01-1 (0.09) | 0.1-1 (0.09) |

In certain aspects, the feedstock comprises ≥75 wt. % Associated Gas, based on the weight of the feedstock, e.g., ≥90 wt. %, or ≥95 wt. %. Associated Gas is typically found with petroleum deposits, e.g., dissolved in the oil or as a free "gas cap" above the oil in a reservoir. In conventional petroleum production, the lack of effective natural transportation facilities, e.g., the lack of natural gas liquefaction and/or pipeline facilities, can result in Associated Gas being stranded at or near the reservoir. This in turn can lead to a need for undesirable natural gas flaring. Moreover, even in locations where pipeline facilities are available, Associated Gas may be excluded from the pipeline because it typically exceeds one or more pipeline specifications, e.g., ≤12 wt. % ethane, ≤5 wt. % propane, ≤2 wt. % butanes, a Wobbe Index of from 49.01 MJ/sm$^3$ to 52.22 MJ/sm$^3$), and a heating value of from 36.07 MJ/sm$^3$ to 41.40 MJ/sm$^3$).

Since methane is not detrimental to the process, and is in at least some aspects beneficial, the invention obviates the need for costly and inefficient cryogenic methane separation facilities, such as one or more conventional cold boxes. Typically, obtaining the feedstock from the source material (e.g., natural gas, such as raw gas) does not include (i) exposing the feedstock, source material, or any intermediate thereof to a temperature ≤−37° C., e.g., ≤−46° C., such as ≤−60° C. Certain aspects of the invention do not include cryogenic processing, e.g., cryogenic methane separation is not used.

The invention is advantageous in remote or under-developed locations, where (i) the lack of cryogenic methane separation facilities limits the utility of conventional natural gas aromatization processes, (ii) the lack of a pipeline or natural gas production infrastructure, may result in significant quantities of light hydrocarbon being flared or burned as fuel, and (iii) Associated Gas remains stranded at a remote location for lack of pipeline facilities or a failure to meet one or more specifications of an available pipeline. Small scale plants using the present process would allow effective recovery of these light hydrocarbon resources as liquid hydrocarbons. The invention is particularly advantageous for upgrading relatively refractory paraffinic hydrocarbon such as ethane. Accordingly, the feedstock can comprise ethane in an amount ≥1 wt. %, e.g., ≥5 wt. %, such as ≥10 wt. %. Suitable feedstock include those containing a major amount of ethane, e.g., ≥50 wt. % ethane, such as ≥75 wt. %, or ≥90 wt. %, or ≥95 wt. %. For example, the feedstock can comprise an amount of ethane in the range of from 1 wt. % to 99 wt. %, such as 5 wt. % to 95 wt. %, or 10 wt. % to 90 wt. %. One representative feedstock comprises (i) ≥10 wt. % ethane, or ≥50 wt. %, or ≥90 wt. %, such as in the range of from 10 wt. % to 99.5 wt. % ethane, with ≥95 wt. % of the balance of the feedstock comprising one or more of methane, propane, and butanes.

Aspects of the invention which include contacting the specified feed with the specified active material to produce aromatics, such as naphtha, BTX, etc., will now be described in more detail. The invention is not limited to these aspects, and this description is not meant to foreclose other aspects within the broader scope of the invention.

Process

In certain aspects, the aromatization reaction is carried out in at least one reaction zone. For example, a light paraffinic hydrocarbon feedstock comprising the $C_{2+}$ non-aromatic hydrocarbon can be contacted with the specified active material that is located in one or more fixed beds in at least one reaction zone.

The aromatic hydrocarbon produced by the aromatization typically comprises single-ring aromatic hydrocarbon, multiple-ring aromatic hydrocarbon and mixtures thereof. Single-ring aromatic hydrocarbon has six or more carbon atoms on an aromatic ring, and is typically selected from the group consisting of benzene, toluene, xylenes, and mixtures of two or more thereof. For example, the single-ring aromatic hydrocarbon can be one or more of benzene, toluene or one or more of the xylene isomers. The multiple-ring aromatic hydrocarbon can be naphthalene, for example.

In certain aspects, the process includes the conversion to aromatic hydrocarbon of at least a portion of the feedstock's non-aromatic hydrocarbon, e.g., dehydrocyclization of paraffinic $C_1$ to $C_5$ hydrocarbon. Typically, the process has selectivity for aromatic hydrocarbon, molecular hydrogen, and optionally additional non-aromatic hydrocarbon. The conversion conditions typically include exposing the feed to a temperature in the range of from 400° C. to 750° C., and a pressure in the range of from 35 kPa to 2200 kPa, e.g., 35 kPa to 1480 kPa. Typically, the process conditions further include a weight hourly space velocity (WHSV)≥0.1 $hr^{-1}$. More typically, the conditions include introducing the feedstock into a reaction zone which has been heated to a temperature in a range of from 400° C. to 630° C., and has a pressure in the range of from about 138 kPa (20 psia) to about 2070 kPa (300 psia), such as a temperature in the range of from 500° C. to 625° C. and a pressure in the range of from 30 psia (207 kPa) to 80 psia (522 kPa). WHSV can be in the range of from 0.1 $hr^{-1}$ to 20 $hr^{-1}$. More typically, the temperature is in the range of from 450° C. to 605° C., the pressure is in the range of from about 207 kPa (30 psia) to about 522 kPa (80 psia), and the weight hourly space velocity (WHSV) is in the range of from 0.1 to 10 $hr^{-1}$. Typically, the WHSV of $C_{2+}$ hydrocarbon (the "$C_{2+}$ WHSV") in the specified aromatization feed with respect to the catalyst is in the range of from 0.1 $hr^{-1}$ to 20 $hr^{-1}$, e.g., 0.2 $hr^{-1}$ to 5 $hr^{-1}$, or 0.3 $hr^{-1}$ to 1 $hr^{-1}$. The $C_{2+}$ WHSV is the hourly rate of the $C_{2+}$ hydrocarbon (in grams per hour) exposed to the catalyst per gram of the catalyst. The reaction is typically endothermic. Generally, the average temperature drop across the reaction zone is ≤600° C., more typically in the range of from 20° C. to 200° C., e.g., in the range of from 50° C. to 150° C.

The process can be carried out using the specified active material, e.g., the specified conversion catalyst (the "catalyst"), in at least one reaction zone. Each reaction zone may have one or more stages containing at least one bed of the catalyst of this invention. The catalyst bed may be one or more of a fixed bed, a moving bed, or fluidized bed. Conventional fixed, moving, and/or fluidized beds may be used in one or more of the reaction zones, but the invention is not limited thereto. Although the catalyst can be present in the reaction zone in the form of a fluidized particulate, the process can alternatively or in addition be carried out with the catalyst in the form of a plurality of catalytic solid bodies, e.g., macrostructures such as extrudates, pellets, etc.

Accordingly, in certain aspects the catalyst resides in one or more fixed catalyst beds in one or more reaction zones wherein the specified feedstock contacts the catalyst under the specified conversion conditions. In a fixed catalyst bed (also called a packed bed), the catalyst bed is "fixed" in the sense that it is substantially immobile with respect to the fixed reference frame during the conversion. The reactor may be, e.g., an adiabatic single bed, a multi-tube surrounded with heat exchange fluid or an adiabatic multi-bed with internal heat exchange, among others. At least one substantially similar second reaction zone may be operated in parallel with the first reaction zone, so that the first reaction zone may be operated in reaction mode while the second reaction zone is operated in regeneration mode, to regenerate the second reaction zone's catalyst. Continuous operation may be carried out by alternating reaction and regeneration modes in the first and second reaction zones.

In other aspects, the process is carried out in a catalyst bed exhibiting catalyst motion during the process, e.g., in a moving bed, a fluidized bed, and ebullating bed, etc. In a moving catalyst bed, particles of the specified catalyst flow into and out of the reaction zone under the influence of an external force such as gravity. The catalyst particles substantially maintain their relative positions to one another during the flow, resulting in a movement of the bed with respect to the fixed reference frame. Average flow of the specified feedstock with respect to the catalyst flow may be concurrent, countercurrent, or cross-current.

An aromatic-containing effluent is conducted away from the reaction zone for recovery of at least a portion of the effluent's aromatics. When the process is operated using the specified feed under the specified conditions, the reaction typically results in (i) ≥20 wt. % conversion of the feed's $C_{2+}$ non-aromatic hydrocarbon, e.g., ≥25%, such as ≥50%, or ≥75%; and (ii) a $C_{3+}$ conversion ≥50%, e.g., ≥75%, or ≥90%, or ≥95%, or ≥98%. The effluent typically includes (i) unreacted feed, including unconverted diluent, and (ii) vapor-phase and/or liquid-phase products of the dehydrocyclization reaction and other reaction pathways. Typically, the effluent does not include solid (e.g., catalyst coke) and/or semi-solid (e.g., catalyst coke precursors) products of dehydrocyclization and other reaction pathways, as these generally remain in the reactor until they are removed during regeneration.

When the feed comprises natural gas, the effluent typically comprises ≥10 wt. % aromatic hydrocarbon, molecular hydrogen, ≥1 wt. % ethane, 1 wt. % to 40 wt. % methane, ≤2 wt. % propane, and ≤1 wt. % butanes.

Since the specified catalyst is more resistant to deactivation and/or has less coke selectivity than conventional hydrocarbon conversion catalysts, the catalyst can be used on-stream for aromatization run lengths greater than 50 hours before catalyst regeneration or rejuvenation is needed (as indicated by an aromatics yield that is less than 50% of the start of run yield), e.g., run lengths greater than 100 hours, or greater than 5 days, or greater than 10 days. For example, it has been found that when using the specified catalyst in the presence of the specified feed there is typically (i) no more than a 5% reduction in yield of aromatic hydrocarbon and (ii) typically no more than a 10% reduction in conversion, after the catalyst has been present in the reaction zone in the presence of the feedstock for a time-on-stream in the reaction zone of 50 hours under the specified process conditions.

When operating under the specified process conditions, the process typically exhibits no more than a 10% reduction in the yield of the aromatic hydrocarbon when the catalyst achieves a time-on-stream in conversion mode of 20 hours from the start of conversion, e.g., ≤7%, such as ≤5%. More typically, the process results in no more than a 10% reduction in the yield of the aromatic hydrocarbon when the catalyst achieves a time-on-stream in conversion mode of 50 hours from the start of conversion, e.g., ≤7%, such as ≤5%.

Certain catalytically active materials which are useful as catalysts for the aromatization will now be described in more detail. The invention is not limited to these catalytically active materials, and this description is not meant to foreclose other active materials within the broader scope of the invention.

Active Materials

Certain aspects of the invention relate to catalytically active materials (e.g., aromatization catalyst) which include a molecular sieve component and a dehydrogenation component, but contain ≤20 wt. % of binder. The term "binder" as used in this description and appended claims includes matrix and other materials which are typically added during manufacturing of conventional molecular-sieve containing catalysts, e.g., (i) as a process-ability aid during extrusion, pelletizing, etc., and/or (ii) to make the catalyst more resistant to temperature and other process conditions employed during hydrocarbon conversion. It has been reported that such binder can have a neutral or even beneficial effect on the use of conventional molecular sieve catalysts in hydrocarbon processing. This has been found to not be the case for the instant active materials when used for hydrocarbon conversion reactions such as aromatization. Accordingly, the instant active materials contain ≤20 wt. % of binder, resulting in decreased selectivity to coke during aromatization in comparison with conventional catalysts, and an increase in run length before catalyst regeneration is needed.

Typically, the active material is substantially free of binder, such as an inorganic binder. For example, the active material can contain ≤1 wt. % of binder, such as ≤0.1 wt. %, based on the weight of the catalyst. The molecular sieve component is typically present in the active material in an amount of ≥80 wt. %, or ≥90 wt. %, or ≥95 wt. %, or ≥98 wt. %, or ≥99 wt. %, based on the weight of the active material. In certain aspects, the molecular sieve component includes aluminosilicate, e.g., ≥90 wt. % of at least one aluminosilicate. The aluminosilicate can be an un-substituted aluminosilicate, a substituted aluminosilicate, or a combination thereof. For example, the aluminosilicate can be in a form where at least a portion of its original metal has been replaced, e.g., by ion exchange, with other suitable metal (typically metal cation) of Groups 1-13 of the Periodic Chart. Typically, the aluminosilicate includes zeolite aluminosilicate, e.g., ≥90 wt. % of at least one zeolite based on the weight of the aluminosilicate. The term zeolite includes those in which at least part of the aluminum is replaced by a different trivalent metal, such as gallium or indium.

The molecular sieve component typically includes ≥90 wt. % of one or more of the specified molecular sieves, e.g., ≥95 wt. %, such as ≥99 wt. %. In certain aspects, the molecular sieve component includes at least one zeolite molecular sieve, e.g., ≥90 wt. % zeolite, such as ≥95 wt. %, based on the weight of the molecular sieve component. Although, the molecular sieve component can consist essentially of or even consist of zeolite, in alternative aspects the zeolite(s) is present in the molecular sieve component in combination with other (e.g., non-zeolitic) molecular sieve. The molecular sieve may be one that is in hydrogen form, e.g., one that has been synthesized in the alkali metal form, but is then converted from the alkali to the hydrogen form and has hydrogen ions. For example, zeolite can be present in hydrogen form, e.g., zeolite synthesized in the alkali metal form, but is then converted from the alkali to the hydrogen form.

In certain aspects, the molecular sieve component is a crystalline aluminosilicate and is present in the catalyst in an amount ≥80 wt. %, or ≥85 wt. %, or ≥90 wt. %, or ≥95 wt. % or ≥99 wt. %, based on the weight of the catalyst. When the molecular sieve component comprises crystalline aluminosilicate, the crystalline aluminosilicate typically has a constraint index of less than 12, preferably, in the range of about 1 to about 12. Typically, the crystalline aluminosilicate is one having a medium pore size and a Constraint Index of less than or equal to about 12. Examples of suitable aluminosilicates include ZSM-5, ZSM-11, ZSM-12, ZSM-21, ZSM-22, ZSM-23, ZSM-35, ZSM-38, ZSM-48 ZSM-50, ZSM-57, and MCM-68, including mixtures and intermediates thereof such as ZSM-5/ZSM-11 admixture. ZSM-5 is described in U.S. Pat. Nos. 3,702,886 and Re. 29,948. ZSM-11 is described in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-21 is described U.S. Pat. No. 4,082,805. ZSM-22 is described in U.S. Pat. No. 4,556,477. ZSM-23 is described in U.S. Pat. No. 4,076,842. ZSM-35 is described in U.S. Pat. No. 4,016,245. ZSM-38 is described in U.S. Pat. No. 4,046,859. ZSM-48 is described in U.S. Pat. No. 4,234,231. ZSM-50 is described in U.S. Pat. No. 4,640,826. ZSM-57 is described in U.S. Pat. No. 4,873,067. TEA-Mordenite is described in U.S. Pat. Nos. 3,766,093 and 3,894,104. MCM-68 is described in U.S. Pat. No. 6,049,018.

The aluminosilicate's silica-to-alumina ($Si:Al_2$) atomic ratio is typically ≥2 molar, e.g., in the range of 10 to 300 molar, or in the range of from 5 to 100 molar. The silica-to-alumina ratio, $Si:Al_2$, is meant to represent the $Si:Al_2$ atomic ratio in the rigid anionic framework of the crystalline aluminosilicate. In other words, aluminum in (i) any matrix or binder, or (ii) in cationic, or other form within the crystalline aluminosilicate's channels is excluded from the $Si:Al_2$ atomic ratio. Aluminosilicates having a higher silica-to-alumina ratio can be utilized when a lower catalyst acidity is desired, e.g., in the range of from 44 to 100 molar, such as from 50 to 80 molar, or 55 to 75 molar.

In certain aspects, the crystalline aluminosilicate has a constraint index in the range of about 1 to 12 and is selected from the group consisting of a MCM-22 family material, ZSM-5, ZSM-11, ZSM-12, ZSM-21, ZSM-22, ZSM-23, ZSM-35, ZSM-38, ZSM-48, ZSM-50, ZSM-57, MCM-68 and mixtures of two or more thereof. Preferably, the aluminosilicate is ZSM-11 or H-ZSM-11 (the acidic form of ZSM-11), and more preferably, the aluminosilicate is ZSM-5 or H-ZSM-5 (the acidic form of ZSM-5). The molecular sieve can have a relatively small crystal size, e.g., small crystal ZSM-5, meaning ZSM-5 has a crystal size ≤0.05 μm, such as in the range of 0.02 μm to 0.05 μm. Small crystal ZSM-5 and the method for determining molecular sieve crystal sizes are disclosed in U.S. Pat. No. 6,670,517, which is incorporated by reference herein in its entirety.

In other aspects, the crystalline aluminosilicate comprises at least one molecular sieve of the MCM-22 family, e.g., MCM-22 alone or in combination with other aluminosilicates, specified above, or other MCM-22 family materials. Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), and ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures of two or more thereof. Related aluminosilicates to be included in the MCM-22 family are UZM-8 (described in U.S. Pat. No. 6,756,030) and UZM-8HS (described in U.S. Pat. No. 7,713,513), both of which are also suitable for use as the molecular sieve component.

Besides the molecular sieve component, the active material further comprises a dehydrogenation component, e.g., an active metal. Even though both the dehydrogenation component and the molecular sieve can contain metal, the dehydrogenation component and the molecular sieve components are substantially different components, and each is present in the active material in the specified amounts. It should also be noted that even though it is believed that the specified active metals are effective for dehydrogenation, this might not always be the case, and the term "active metal" should not be interpreted as requiring effectiveness for dehydrogenation when present in a particular active material. The dehydrogenation component typically comprises at least one element from Group 5 to 15 of the Periodic Chart, and generally comprises one or more metallic elements in these groups. Typically ≥50 wt. % of the dehydrogenation component comprises the active metal, e.g., ≥75 wt. %, such as ≥90 wt. %, or ≥95 wt. %, based on the weight of the dehydrogenation component. Preferably, the active metal is a first active metal selected from the group consisting of and includes one or more of zinc, gallium, indium, copper, silver, tin, iron, cobalt, nickel, gold, manganese, chromium, molybdenum, tungsten, and mixtures of two or more thereof. Preferably, the first active metal is one or more of Mo, W, Zn, and Ga.

In certain aspects, the dehydrogenation component further comprises at least one second active metal in addition to the first active metal. The second active metal is different from the first active metal. The second active metal is selected from the group consisting of and includes one or more of phosphorus, platinum, palladium, lanthanum rhenium, and mixtures of two or more thereof. For example, the second active metal can be phosphorus.

In certain aspects, the active material contains at least about 0.005 wt. % of the first active metal, or in the range from about 0.005 wt. % to about 4.0 wt. %, or from about 0.01 wt. % to about 3.0 wt. %, based on the weight of the catalyst. When the second active metal is present, the active material can contain the second active metal in an amount, e.g., in a range from 0 wt. % to about 5.0 wt., or from about 0.005 wt. % to about 4.0 wt. %, or from about 0.01 wt. % to about 3.0 wt., based on the weight of the active material.

Not being bound by any theory, it is believed that the higher catalyst activity provided by the increased molecular sieve (preferably, aluminosilicate) content is modulated by the presence of the dehydrogenation component (e.g., the first active metal and optionally, the second active metal), leading to decreased coke selectivity and/or increased cycle length when the catalyst is used in a process for conversion of a light paraffinic hydrocarbon feedstock in a fixed bed reactor.

Although it is not required, the active material optionally includes binder (e.g., matrix) but in an amount typically ≤20 wt. % based on the weight of the catalyst, e.g., ≤15 wt. %, such as ≤10 wt. %, or ≤5 wt. %, or ≤1 wt. %, or ≤0.1 wt. %. When used, binder can include inorganic material, e.g., clays and/or inorganic oxides. Suitable inorganic binders include alumina, silica, silica-alumina, titania, zirconia, magnesia, tungsten oxide, ceria, niobia, and mixtures of two or more thereof. Matrix can include naturally occurring materials and/or materials in the form of gelatinous precipitates or gels including mixtures of silica and metal oxides. Clays may also be included with the oxide type binders to modify the mechanical properties of the catalyst or to assist in its manufacture. Optionally, the binder may include one or more substantially inactive materials, e.g., diluent to control the amount of conversion so that products may be obtained economically and orderly without employing other means for controlling the rate of reaction. These materials may be incorporated into naturally occurring clays, e.g., bentonite and kaolin, to improve thermal and strength properties (e.g., crush strength) of the catalyst under catalytic conversion conditions. The binder may include other active materials, such as synthetic or naturally occurring aluminosilicate.

In certain aspects, the crystalline aluminosilicate and the active metal together comprise ≥85 wt. % of the active material, or ≥90 wt. %, or ≥95 wt. % or ≥99 wt. %. For example, the active material can be one where (i) ≥95 wt. % of the molecular sieve component comprises aluminosilicate, e.g., ≥99 wt. %, such as ≥99.9 wt. %, or even about 100 wt. %, (ii) ≥95 wt. % of the dehydrogenation component comprises active metal, e.g., ≥99 wt. %, such as ≥99.9 wt. %, or even about 100 wt. %, wherein the active metal is one or more of Ga, In, Zn, Cu, Re, Mo, and W, and (iii) the molecular sieve component and dehydrogenation component together constitute ≥95 wt. % of the active material, e.g., ≥99 wt. %, such as ≥99.9 wt. %, or even about 100 wt. %.

When used as catalyst in the specified hydrocarbon conversion, the active material can have any convenient form or morphology. For example, in certain aspects, the catalyst has the form of as-synthesized particles of the active material, e.g., a plurality of crystalline particles which comprise the crystalline molecular sieve and the active metal. The catalyst particles can used as-synthesized. Alternatively or in addition, the catalyst particles can be, e.g., ground and sieved into a desired particle-size range; composited (with or without grinding and/or sieving) with binder to produce a solid catalytic body (e.g., a microstructure); self-bound to produce a microstructure; etc. The specified catalyst, as-synthesized, can be further processed (e.g., by grinding and sieving) into a wide range of sizes, e.g., (i) a powder having an average size ≤10 micrometers ("µm"), e.g., ≤2 µm, or ≤500 nm, or ≤200 nm, or ≤100 nm, or in the range of from 50 nm to 10 µm; (ii) a particulate having an average size ≥10 µm, e.g., ≥100 µm, such as ≥300 µm, or in the range of from 50 µm to 500 µm. Those skilled in the art will appreciate that there is considerable overlap in terminology (powder vs. particulate) for catalyst having average sizes spanning the range from about 1 nm to about 1 mm. In other aspects, the specified catalyst has the form of a solid body or plurality thereof. For example, the specified catalyst can have the form of a macrostructure or plurality of macrostructures, including those having a size ≥0.01 mm in at least one dimension, e.g., ≥0.1 mm, or ≥1 mm. Examples of such macrostructures include those in the form of spheroids, extrudates (e.g., cylindrically-symmetric extrudates), pellets, fibers, thin films, etc. Conventional methods can be used for manufacturing a macrostructure comprising the specified catalyst, but the invention is not limited thereto. In certain aspects, the specified catalyst is self-bound, with the self-bound catalyst being in any convenient form during use for hydrocarbon conversion, e.g., in the form of a particulate which includes a plurality of self-bound catalyst particles, a self-bound porous macrostructure, a plurality of porous macrostructures, etc. Conventional methods can be used for making the specified catalyst in a self-bound form e.g., those disclosed in U.S. Pat. Nos. 5,510,016 and 6,787,623, which are incorporated by reference herein in their entireties, but the invention is not limited thereto. In any of the foregoing forms, e.g., crystalline particulate, bound composite, particulate of self-bound catalyst, self-bound macrostructure, etc., the specified catalyst typically has a surface area, as measured by nitrogen physisorption, in the range of from 100 $m^2$/g to 600 $m^2$/g, e.g., in the range of from 200 $m^2$/g to 500 $m^2$/g.

It was expected that improved performance during hydrocarbon conversion (e.g., decreased coke selectivity and/or increased run-lengths between regeneration intervals) would be achieved with a conventional catalyst in the form of a porous macrostructure comprising (i) ≥20 wt. % of binder and (ii) particles of the crystalline molecular sieve particles impregnated with metal. It was believed that the binder would provide a substrate to which coke and coke precursors would adhere during use, leaving active sites associated with the molecular sieve particles available for continued hydrocarbon conversion. Surprisingly, it has been found that this is not the case: better performance is achieved when the specified catalyst contains ≤20 wt. % of binder. Even more surprising, it has been discovered that the specified catalyst in self-bound form performs better than "as synthesized" catalyst with or without binder. This performance improvement exhibited by the specified catalyst in self-bound form over that of the "as synthesized" catalyst is observed even when both have the same morphology. For example when (i) the "as synthesized" catalyst is ground and sieved to produce a particulate in a pre-selected particle size range and (ii) the "as synthesized" catalyst is first formed into a self-bound macrostructure which is then ground and sieved to produce a particulate in the same particle size range (e.g., 200 μm to 400 μm), the second particulate exhibits better performance than the first.

Particular aspects of the catalyst will now be described in more detail.

Particular Aspects of the Catalyst

In particular aspects, ≥80 wt. % of the active material comprises (i) at least one active metal and (ii) at least one molecular sieve having a framework of interconnected atoms. The framework defines an outer surface of the molecular sieve and a plurality of pores located within the molecular sieve. A feature of molecular sieve of these aspects is that at least some of the molecular sieve's pores have an average pore size in the range of from 4 Å to 7 Å. Typically, the pores are not completely enclosed by the molecular sieve's outer surface. Instead, at least some of the pores typically have one or more pore openings through the outer surface. Another feature of the molecular sieve of these aspects is that ≥90 wt. % of the active metal is located in those pores having an average pore size in the range of from 4 Å to 7 Å, e.g., ≥95 wt. %, such as ≥99 wt. %, or ≥99.9 wt. %. Yet another feature of the molecular sieve of these aspects is that ≤10 wt. % of the active metal is located proximate to the outer surface, e.g., ≤5 wt. %, such as ≤1 wt. %, or ≤0.1 wt. %. In this context, "proximate to" means within about 10 Å of the outer surface, e.g., within 5 Å, such as within 2.5 Å. More typically, the molecular sieve of these aspects has at least one set of pores of substantially uniform size extending through the molecular sieve, wherein geometric mean of the cross-sectional dimensions of each of the pores is ≥4 Å, or ≥5 Å, or ≥5.3 Å, e.g., ≥5.4 Å such as ≥5.5 Å, or in the range of 5 Å to 7 Å, or 5.4 Å to 7 Å.

Typically, the active material of these aspects include ≥90 wt. % of one or more molecular sieves and ≥0.005 wt. % of one or more of the active metals, e.g., ≥0.005 wt. % of one or more of the active metals in carbidic form, wherein the molecular sieve has a Constraint Index in the range of from 1-12, e.g., 2-11. When the molecular sieve and active metal together constitute less than 100 wt. % of the active material, ≥90 wt. % of the remainder of the active material can include binder, such as ≥99 wt. % of the remainder, provided the total amount of binder in the active material is ≤20 wt. %. A feature of the active material of these aspects is that it includes ≤10 wt. % of metal in any form other than (A) framework metal if any (e.g., framework aluminum atoms) and (B) the active metal located in the pores of the molecular sieve. Since the active metal is primarily (e.g., more than 50 wt. %, such as more than 75 wt. %, or more than 90 wt. %) located in the pores of the molecular sieve, the active material of these aspects can be referred to as an "embedded catalyst". When the molecular sieve is a silicoaluminate such as ZSM-5, e.g., ZSM-5 in hydrogen form ("HZSM-5"), the embedded catalyst can be represented symbolically by [metal]@ZSM-5, [metal]@HZSM-5, and the like. For example, when the active metal is molybdenum and the molecular sieve is HZSM-5, the embedded catalyst can be represented symbolically by Mo@HZSM-5. This symbolic representation is different from that used to represent conventional metal-impregnated ZSM-5, e.g., Mo-impregnated ZSM-5, which typically has the symbolic representation Mo/ZSSM-5 or Mo-ZSM-5.

The conversion catalyst typically includes the molecular sieve in an amount ≥85 wt. %, based on the weight of the conversion catalyst, e.g., ≥90 wt. %, such as ≥95 wt. %, or in the range of from 85 wt. % to 99.9 wt. %. The molecular sieve of these aspects can include, e.g., ≥90 wt. % of at least one of the specified aluminosilicates.

Besides the molecular sieve, the catalysts of these aspects includes at least one active metal in amount ≥0.005 wt. %, based on the weight of the catalyst. The active metal in these aspects is typically one or more of Ga, In, Zn, Cu, Re, Mo, W, La, Fe, Ag, Pt, and Pd, in neutral form and/or one or more oxides, sulfides and/or carbides of these metals. For example, the active metal can be one or more of Mo, Ga, Zn. The active metal can be, e.g., one or more carbidic molybdenum compounds, such as one or more molybdenum carbides and/or one or more molybdenum oxycarbides.

Typically, the active material of these aspects includes ≥0.01 wt. % of the active metal, e.g., ≥0.1 wt. %, such as ≥0.5 wt. %, or ≥1 wt. %, or ≥5 wt. %, or ≥10 wt. %. These weight percents represent the weight of the metal, not the weight of the active-metal compound containing the active metal. For example, the active material can comprise ≥1 wt. % of Mo in the form of $MoO_3$, such as ≥5 wt. %, or ≥10 wt. %. In certain aspects, (i) ≥99 wt. % of the active metal is one or more of Ga, Zn, Mo, and In, e.g., ≥99 wt. % of Mo in the form of one or more carbidic molybdenum compounds, such as one or 99 wt. % of Mo in the form of more molybdenum carbides and/or one or more molybdenum oxycarbides and (ii) ≥99 wt. % of the molecular sieve is ZSM-5-type zeolite. One typical active material of these aspects comprises ZSM-5, e.g., HZSM-5, and at least one of (i) molybdenum carbide, and (ii) molybdenum oxycarbide ("Catalyst X"), wherein the ZSM-5 and the molybdenum compound together comprise ≥80 wt. % of the active material, typically ≥90 wt. %, or ≥95 wt. %, or ≥99 wt. %. Mo is substantially the sole active metal of Catalyst X.

As in the preceding aspects, the active material of these aspects can contain binder in an amount ≤20 wt. % based on the weight of the active material, e.g., ≤15 wt. %, such as ≤10 wt. %, or ≤5 wt. %, or ≤1 wt. %, or ≤0.1 wt. %. For example, in any aspect ≥95 wt. % of the specified active material's molecular sieve can be self-bound molecular sieve, e.g., ≥95 wt. % can be self-bound ZSM-5, and in particular self-bound, small crystal ZSM-5.

Aspects of the invention relating to making the active material of any of the preceding aspects will now be described in more detail. The invention is not limited to these aspects, and this description is not meant to foreclose other aspects in the broader scope of the invention.

Method of Making the Active Material

In certain aspects, the active material is produced by contacting a molecular sieve with a source of the active metal. The molecular sieve can be, e.g., a crystalline aluminosilicate, which has a constraint index of less than or equal to about 12, preferably in the range of about 1 to about 12, more preferably, a crystalline aluminosilicate comprising ZSM-5 or ZSM-11. The molecular sieve is contacted with a source of a first active metal and optionally a source of a second active metal under conditions sufficient to deposit the first (and optionally second) active metal on, in, or proximate to the molecular sieve.

If both active metals are used, the first active metal is different from the second active metal. The first active metal is typically selected from the group consisting of zinc, gallium, copper, indium, silver, tin, iron, cobalt, nickel, gold, manganese, chromium, molybdenum, indium, molybdenum tungsten, and mixtures of two or more thereof. The second active metal is typically selected from the group consisting of phosphorus, platinum, palladium, lanthanum rhenium, and mixtures of two or more thereof.

The first active metal and the optional second active metal may be deposited on, in, or proximate to the molecular sieve by any convenient method. Conventional methods can be used, e.g., by impregnating the first active metal and optionally the second active metal onto the external surface of the molecular sieve, but the invention is not limited thereto. For example, the first active metal and optionally the second active metal may be dissolved in a liquid carrier, for example an aqueous or organic carrier, mixed with the catalyst, and then dried by evaporation or vacuum distillation. Other conventional methods, e.g., incipient wetness, also can be used. Certain non-limiting examples of the conditions effective to deposit the first active metal and optionally the second active metal on the molecular sieve, preferably the crystalline aluminosilicate, are set forth in the Examples.

The active metal used for producing the active material can be, e.g., in the form of a neutral metal and/or one or more oxides, sulfides and/or carbides of metal. For example, non-limiting suitable sources of zinc are selected from the group consisting of zinc nitrate, zinc titanate, zinc silicate, zinc borate, zinc fluorosilicate, zinc fluorotitanate, zinc molybdate, zinc chromate, zinc tungstate, zinc zirconate, zinc chromite, zinc aluminate, zinc phosphate, zinc acetate dihydrate, diethyl zinc, zinc 2-ethylhexanoate, and mixtures of two or more thereof. Suitable lanthanum sources include a lanthanum salt, a lanthanum nitrate, or a mixture thereof.

Particular aspects for making the catalyst will now be described in more detail.

Particular Aspects for Making the Active Material

In particular aspects, the conversion catalyst is produced from the specified synthesis mixture under hydrothermal synthesis conditions. Conventional hydrothermal synthesis conditions can be used, but the invention is not limited thereto. The synthesis mixture comprises water, an aluminum source, a templating agent, and substantially one source of silicon. Typically, the synthesis mixture includes nitrate of aluminum and/or aluminate of at least one alkali metal; hydroxide, e.g., hydroxide of ammonium and/or hydroxide of at least one second alkali metal; water; oxygenate, such as alcohol, e.g., ethanol; and a templating agent such as TPABr, TPAOH, etc. A feature of the specified synthesis mixture of these aspects is that it further comprises a constituent that is substantially the synthesis mixture's sole source of silicon. In certain aspects, (i) ≥90 wt. % of the silica source comprises $SiO_2$ impregnated with oxide of at least one metal selected from Groups 3 to 13 of the Periodic Chart (the active metal), e.g., ≥95 wt. %, such as ≥99 wt. %, or ≥99.9 wt. %, and (ii) the combination of the aluminum source(s), any hydroxide, the water, any alcohol, the templating agent, and any other components of the synthesis mixture does not contain an appreciable amount of silicon or compounds thereof. In this context, less than an appreciable amount means that there is ≤0.1 wt. % of silicon (including silicon present in silicon-containing compounds) in the combination of the aluminum source, any hydroxide, any alcohol, the water, the templating agent, and any other components of the synthesis mixture, e.g., ≤0.01 wt. %, such as ≤0.001 wt. %, or ≤0.0001 wt. %.

The silica source typically comprises a siliceous material and one or more metals selected from Groups 3 to 13 of the Periodic Chart. The metal or metals are typically in the form of one or more metal compounds, e.g., one or more metal oxides. Suitable siliceous materials include porous $SiO_2$. Typically, the metal is located on, in, or proximate to the siliceous material. The term "located on or in" includes, e.g., forms in which the metals and/or compounds thereof are bound to the siliceous material, e.g., via one or more chemical bonds, such as via one or more hydrogen bonds. For example, suitable silica sources include $MoO_3$ and/or $WO_3$ bound via one or more hydrogen bonds to porous $SiO_2$, including those bound via one or more OH groups which are themselves bound to the $SiO_2$. "Proximate to" in this context means within about 10 Å of the $SiO_2$, e.g., within 5 Å, such as within 2.5 Å. Conventional methods can be used to prepare the silica source, but the invention is not limited thereto. Suitable conventional methods of locating the metal, metals, or compounds thereof, on, in, or proximate to the siliceous material include impregnation, incipient wetness, co-precipitation, evaporation, spray drying, sol-gel synthesis, ion exchange, chemical vapor deposition, diffusion, and even physical mixing of precursor species in an appropriate chemical state. When impregnation is used, e.g., the impregnation of $MoO_3$ into porous $SiO_2$, this can be carried out by contacting the porous $SiO_2$ with a solution comprising one or more molybdenum salts, such as ammonium hexamolybdate. Impregnated $SiO_2$ when used, is typically dried, and optionally calcined, before it is added to the synthesis solution.

Convention templating agents can be used for directing the structure of synthesis product toward the desired molecular sieve, but the invention is not limited thereto. When the desired molecular sieve includes ZSM-5, the templating agent can include, e.g., one or more of TPAOH, TPABr, etc. Hydroxide, e.g., ammonium hydroxide, is typically used to regulate to synthesis mixture's pH (e.g., its basicity) so that the silica source is gradually dissolved over the course of the synthesis time. While not wishing to be bound by any theory or model, it is believed that particulate formed during synthesis from metal contained in the silica source, e.g., particulate of $MoO_3$, serve as a substrate for nucleating the desired molecular sieve.

When producing Catalyst X, the synthesis mixture typically comprises, consists essentially of, or even consists of an aluminum source comprising nitrate of aluminum and/or aluminate of at least one alkali metal; hydroxide comprising hydroxide of ammonium and/or hydroxide of at least one second alkali metal; water; ethanol; a templating agent such as TPAOH; and one source of silicon, wherein (i) ≥90 wt. % of the silica source comprises $SiO_2$ impregnated with $MoO_3$, e.g., ≥95 wt. %, such as ≥99 wt. %, or ≥99.9 wt. %, and (ii) the aluminum source, the hydroxide, the water, the ethanol, the templating agent, and other components of the synthesis mixture if any together comprise ≤0.1 wt. % of oxide of silicon, e.g., ≤0.01 wt. %, such as ≤0.001 wt. %, or ≤0.0001 wt. %. Except for the features that (i) they do not in combination contain an appreciable amount of silicon or compounds thereof, and (ii) they direct the molecular sieve structure during hydrothermal synthesis to the desired structure, e.g., to ZSM-5, the choices of the aluminum source, the hydroxide, the templating agent, the alcohol source, and the source of the water are not critical. For example, the aluminum source is typically aluminum nitrate. Although the hydroxide is typically ammonium hydroxide, the hydroxide can alternatively or in addition include hydroxide of at least one second alkali metal, e.g., one having the formula M'OH, where M' is Na and/or K. Optionally, M is not the same as M', but typically they are the substantially the same alkali metal. For Catalyst X, the templating agent is typically tetrapropylammonium OH ("TPAOH").

Those skilled in the art will appreciate that the relative amounts of the aluminum source, the hydroxide, the templating agent, the sole silicon source, the ethanol, and the water are selected to gradually dissolve the silica source and to achieve the desired stoichiometry of the desired molecular sieve and active metal. For example, for Catalyst X the synthesis mixture typically comprises per mole of $Al(NO_3)_3$: 10 to 60 moles of $MoO_3$-impregnated $SiO_2$, such as about 40 moles; 100 moles to 500 moles of $NH_3OH$, such as about 300 moles; 10 moles to 50 moles of TPAOH, such as about 30 moles; 50 moles to 200 moles of ethanol, e.g., about 100 moles; and 100 moles to 3000 moles of water, such as about 1000 moles.

The synthesis of catalyst X can be carried out as follows. The aluminum source is dissolved in a mixture of the water and the ethanol. This solution is agitated (e.g., stirred) while adding the silica source. The templating agent is gradually added (e.g., drop-wise). This precursor mixture is agitated more vigorously (e.g., stirred more vigorously) at a temperature of about 25° C. for about four hours to about eight hours, e.g., about six hours. Afterward, the hydroxide is added to the stirred mixture, followed by 10 minutes to 60 minutes of additional stirring, e.g., about 30 minutes to produce the synthesis mixture. Any suitable vessel can be used for preparing the synthesis mixture, e.g., an autoclave. The synthesis mixture is maintained at a temperature in the range of from 170° C. to 190° C., e.g., about 180° C. under effective hydrothermal synthesis conditions for a time sufficient to form the Catalyst X, typical a time in the range of about 90 hours to about 150 hours, typically about 120 hours. The hydrothermal synthesis can be carried out in a Teflon-lines, stainless steel autoclave, for example. When the metal of the silica source is Mo, the resulting Catalyst X precursor is typically is in the form of crystalline Mo-ZSM-5 having a long axis of at least $1\times10^{-6}$ meters. By virtue of its larger size, the Catalyst X precursor can be readily separated from other products of the hydrothermal synthesis such as analcime and α-quartz, although this is not required.

The catalyst precursor of these aspects is activated to produce the specified conversion catalyst, e.g., to produce Catalyst X. The term "activation" means at least converting into catalytically active form, e.g., into carbidic form (carbide and/or oxycarbide), at least a portion of those metals or metal oxides in the catalyst precursor which are derived from the silica source (the active metal). Activation typically includes drying the catalyst precursor, calcining the dried precursor, and carburizing the calcined catalyst precursor. One or more optional treatments, e.g., to substitute hydrogen atoms for at least a portion of any alkali metal atoms present in the conversion catalyst or catalyst precursor can be carried out if desired. Those skilled in the art will appreciate that conventional drying, calcining, carburizing, and hydrogen substitution can be used, but the invention is not limited thereto. Suitable procedures described in U.S. Pat. Nos. 7,728,186 and 8,841,227, the specifications of which are incorporated by reference herein in their entireties. The following procedures are typical for producing Catalyst X from the Catalyst X precursor.

Drying can be carried out by exposing the catalyst precursor to a substantially non-reacting environment at the drying temperature, e.g., a temperature in the range of about 110° C. to 150° C. for a time in the range of from 8 hours to 16 hours, e.g., about 12 hours. The non-reacting environment can be established by providing a flow of a drying gas, e.g., air, molecular nitrogen, etc. Calcining can be carried out by espousing the catalyst to an oxidizing environment such as air and exposing the catalyst precursor to a gradually increasing temperature. For example, the dried catalyst precursor can be exposed to an temperature which increases from 25° C. at a rate of about 0.5° C. to 5° C. per minute until a temperature of 550° C. is achieved. After holding this temperature substantially constant for a time sufficient to remove any remaining templating agent from the molecular sieve, typically from 1 hour to about 10 hours, the temperature gradually decreased at a rate of about 0.5° C. to 5° C. per minute until a desired temperature (e.g., ambient temperature) is achieved. Carburization can be carried out by exposing the calcined precursor to a gradually increasing temperature (e.g., at a rate of about 5° C. per minute) in the presence of a flow of inert gas, e.g., molecular nitrogen and/or argon, until a temperature of about 550° C. is achieved. With the temperature at about 550° C., a flow of a carburizing gas, e.g., methane or a methane-molecular hydrogen mixture, is substituted for at least a portion of the inert gas flow. The temperature is again increased, e.g., at a rate of about 10° C. per minute until a temperature of about 650° C. is achieved. The carburizing precursor is exposed to this temperature of at least about ten minutes to produce the catalyst, e.g., Catalyst X.

The catalyst and/or precursor thereof can be subjected to one or more treatments. For example, at least a portion of any alkali metal (e.g., Na) on Catalyst X can be removed by contacting Catalyst X and/or precursor thereof with an ammonium halide, e.g., $NH_4Cl$. Other treatments include selectivation treatment to increase selectivity for producing desired aromatic hydrocarbon compounds such as para-xylene. For example, the selectivation can be carried out before introduction of the conversion catalyst into the reactor and/or in-situ in the reactor, e.g., by contacting the conversion catalyst with a selectivating agent, such as at least one organosilicon compound (typically with a liquid carrier and subsequently calcining the conversion catalyst at a temperature of 350° C. to 550° C. This selectivation procedure can be repeated two or more times and alters the diffusion characteristics of the conversion catalyst such that the formation of para-xylene over other xylene isomers is favored. Such a selectivation process is described in detail in U.S. Pat. Nos. 5,633,417 and 5,675,047.

EXAMPLES

The invention will now be more particularly described with reference to the following Examples. Numerous modifications and variations are possible and it is to be understood that within the scope of the appended claims, the invention may be practiced otherwise than as specifically described herein.

Alpha Value

The alpha value is a measure of the cracking activity of a catalyst and is described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test used herein included a constant temperature of 538° C. and a variable flow rate as described in detail in the Journal of Catalysis, Vol. 61, p. 395 (1980).

Materials and Preparations

H-ZSM-5 is used as the starting material to synthesize the catalysts of the Examples. As used in the Examples, the percentages of metal, i.e., gallium (Ga), zinc (Zn), and phosphorus (P), are in weight percent, which is based on the weight of the catalyst. Metal addition to H-ZSM-5 extrudate containing a binder is completed by conventional incipient wetness. Zinc nitrate and gallium nitrate are used as precursors for metal addition. Solutions of the nitrate salt are prepared by dissolving the appropriate amount of metal salt into deionized water. The solution volume required for incipient wetness impregnation is determined using the absorption factor for the catalyst (g $H_2O$/g catalyst). The metal salt solution is distributed over the aluminosilicate and left at ambient conditions for 1 hour, followed by drying at 250° F. (121° C.) for 6 hours in flowing air (5 vol. air/vol. solids/min.). The resulting solids is treated at 1000° F. (538° C.) for 3 hours in flowing air (5 vol. air/vol. solids/min.). Table 2 shows the properties of the catalysts that are tested.

TABLE 2

| Sample | Metal Loading (wt. %) | Wt. % Aluminosilicate (Zeolite) | Wt. % Binder | Alpha Value (prior to metal addition) |
|---|---|---|---|---|
| A | 1.5% Ga | 100 | None | 460 |
| B | 1.5% Ga | 65 | 35% silica | 670 |
| C | 1.5% Ga | 65 | 35% alumina | 430 |
| D | 1.5% Ga | 80 | 20% alumina | 1200 |
| E | 3% Zn | 100 | None | 460 |
| F | 3% Zn | 65 | 35% silica | 670 |
| G | 3% Zn | 80 | 20% alumina | 1200 |
| H | 1.5% Zn | 100 | None | 460 |
| I | 1.5% Zn | 65 | 35% alumina | 430 |
| J | 1.5% Zn/ 1% P | 65 | 35% alumina | 430 |
| K | 1% Zn | 100 | None | 460 |
| L | 1% Zn/ 1% P | 100 | None | 460 |
| M | 3% Zn | 65 | alumina | 460 |
| N | 3% Zn | 100 (Crystalline Zeolite Powder) | None | 460 |

Metal-containing H-ZSM-5 catalysts are tested for the conversion of a model natural gas feed (46/24/19/11 vol./vol. of $C_1:C_2:C_3:C4$ alkanes) and the results are shown in FIGS. 1 to 4.

The effect of the amount of binder in the catalyst on the yield of naphtha from natural gas conversion at 550° C. is shown by the Examples of FIGS. 1-4. For the samples tested, the naphtha yield is maintained for a greater length of time for catalysts which contain little or no binder as compared to the catalysts with an alumina or a silica binder. The stabilization of the naphtha yields enables the catalyst cycle length to be increased by at least 48 hours. This increase is significant considering that the cycle length of the zinc-containing catalysts with an alumina binder is only 150-160 hours.

Figure 1:
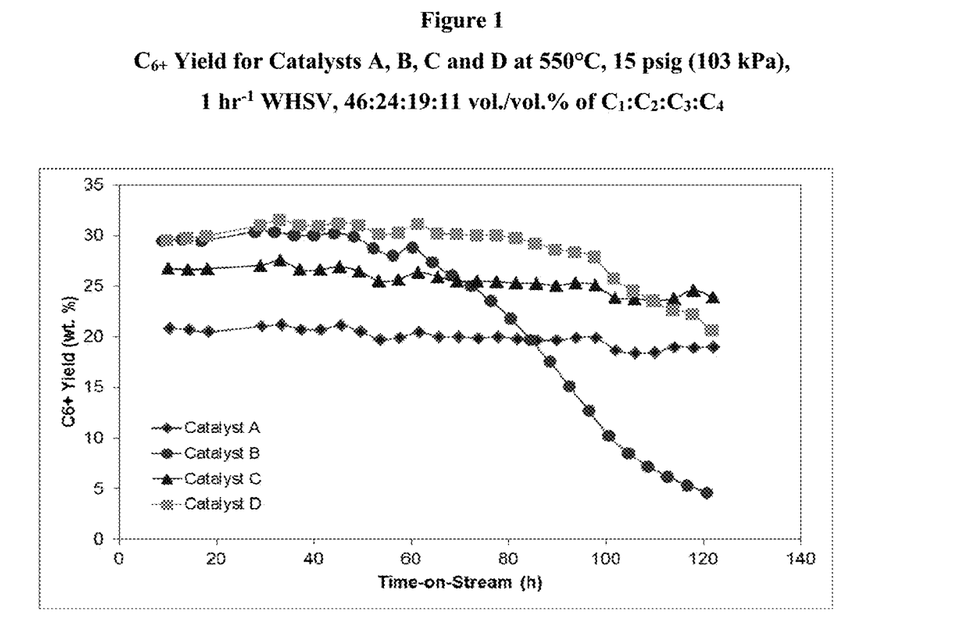
FIG. 1 illustrates the yields of $C_{6+}$ hydrocarbons for the catalytic conversion of a model light paraffinic hydrocarbon feedstock at 550° C., 15 psig (103 kPa), 1 WHSV. The model light paraffinic hydrocarbon feedstock comprises 46 vol./vol. % of methane, 24 vol./vol. % of ethane, 19 vol./vol. % of propane and 11 vol./vol. % of C$_4$ alkane and is contacted with Catalysts A, B, C and D to form a product comprising C$_{6+}$ hydrocarbon.
Figure 2:
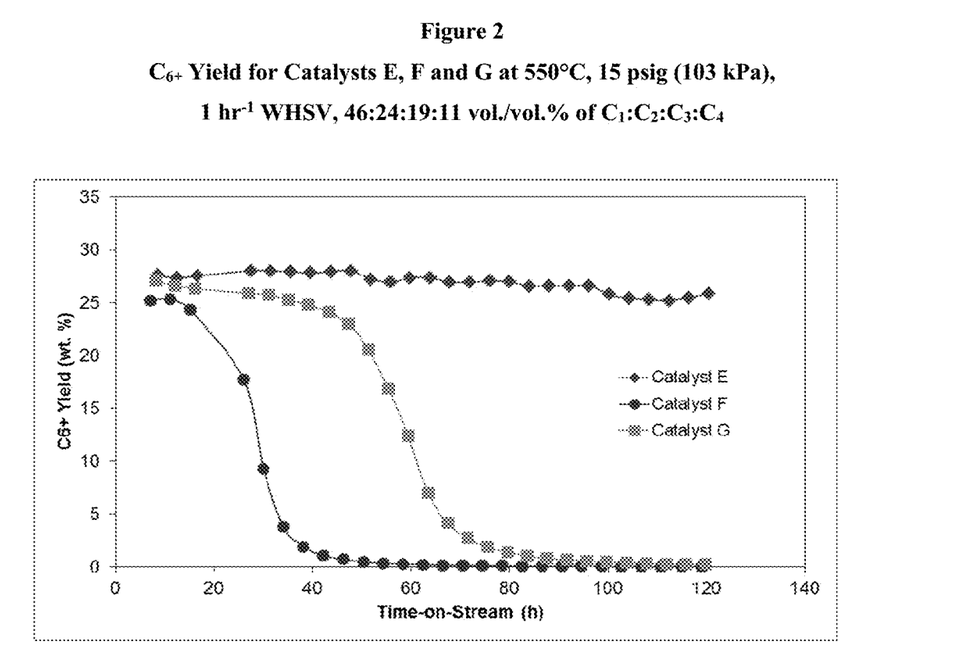
FIG. 2 illustrates the yields of C$_{6+}$ hydrocarbons for the catalytic conversion of a model light paraffinic hydrocarbon feedstock at 550° C., 15 psig (103 kPa), 1 WHSV. The model light paraffinic hydrocarbon feedstock comprises 46 vol./vol. % of methane, 24 vol./vol. % of ethane, 19 vol./vol. % of propane and 11 vol./vol. % of C$_4$ alkane and is contacted with Catalysts E, F and G to form a product comprising C$_{6+}$ hydrocarbon.
Figure 3:
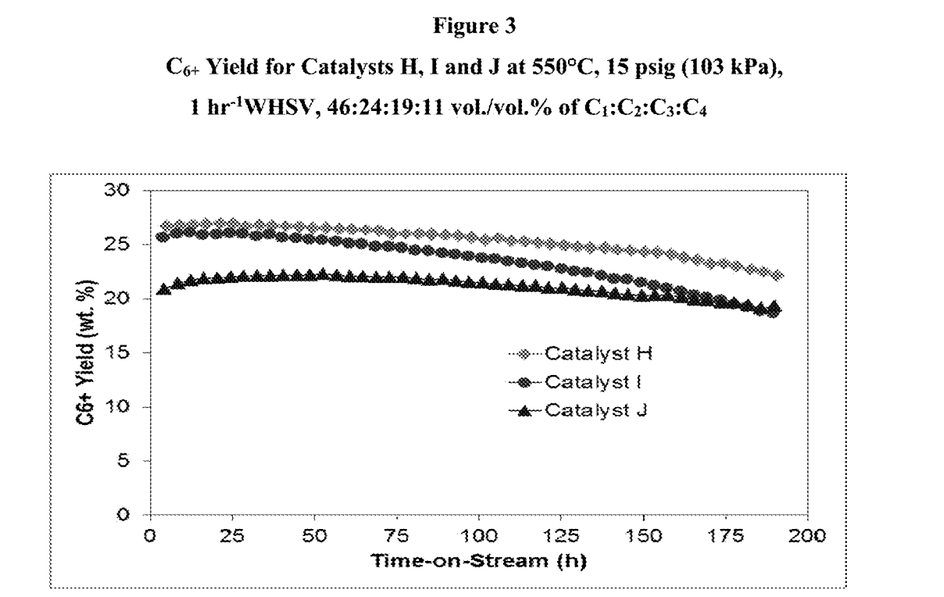
FIG. 3 illustrates the yields of C$_{6+}$ hydrocarbons for the catalytic conversion of a model light paraffinic hydrocarbon feedstock at 550° C., 15 psig (103 kPa), 1 WHSV. The model light paraffinic hydrocarbon feedstock comprises 46 vol./vol. % of methane, 24 vol./vol. % of ethane, 19 vol./vol. % of propane and 11 vol./vol. % of C$_4$ alkane and is contacted with Catalysts H, I and J to form a product comprising C$_{6+}$ hydrocarbon.
Figure 4:
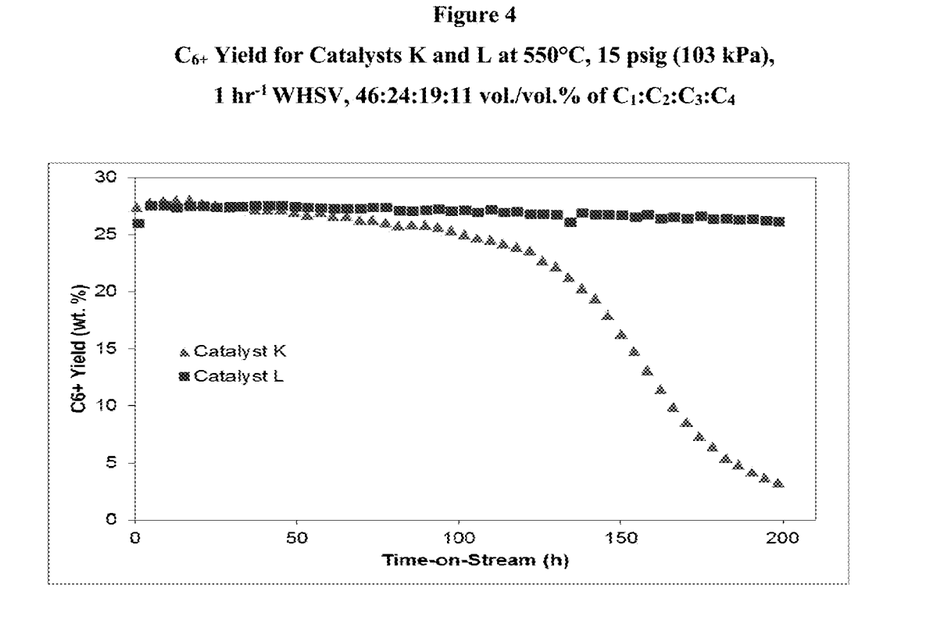
FIG. 4 illustrates the yields of C$_{6+}$ hydrocarbons for the catalytic conversion of a model light paraffinic hydrocarbon feedstock at 550° C., 15 psig (103 kPa), 1 WHSV. The model light paraffinic hydrocarbon feedstock comprises 46 vol./vol. % of methane, 24 vol./vol. % of ethane, 19 vol./vol. % of propane, and 11 vol./vol. % of C$_4$ alkane and is contacted with Catalysts K and L to form a product comprising C$_{6+}$ hydrocarbon.
Figure 5:
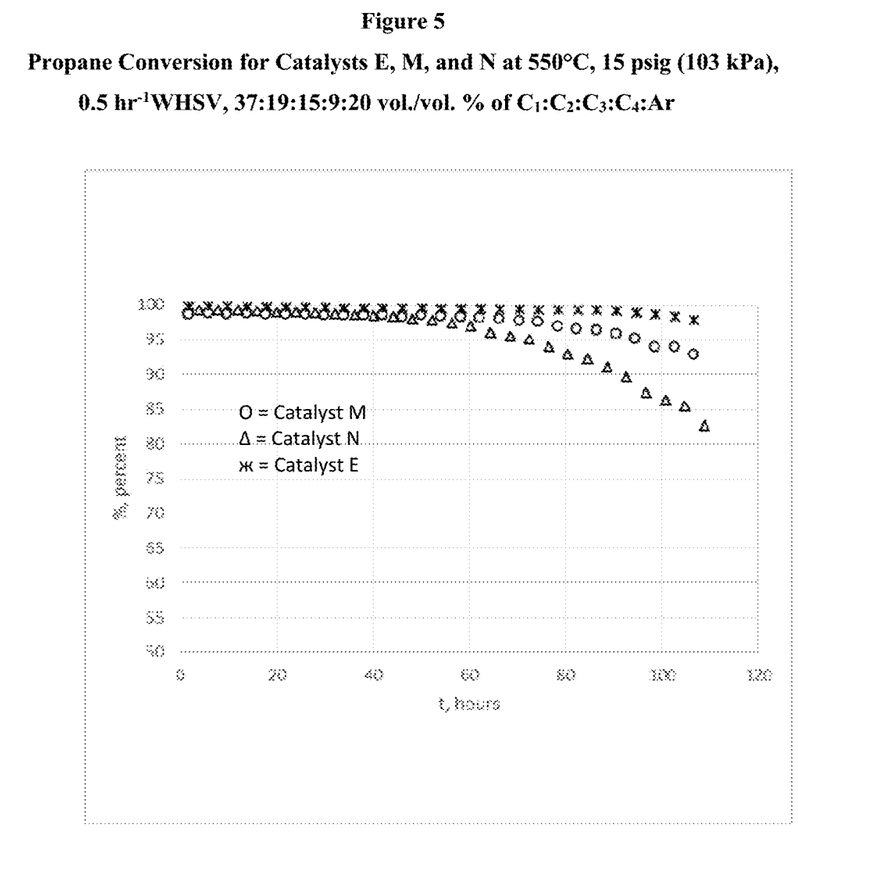

The Examples of FIG. 5, are carried out by exposing the indicated catalysts to the indicated feed under the indicated process conditions, to achieve a substantially constant naphtha yield of about 25%. These Examples show the advantage of using the specified catalyst in self-bound form (Catalyst E) over both Catalyst M (35% binder) and Catalyst N (particulate of as-synthesized crystalline catalyst). In the Examples of FIG. 5, Catalysts E, M, and N each have the morphology of a particulate (a plurality of particles), and each of the particulates (Catalyst E, M, and N) has substantially the same average particle size.

Certain embodiments and features have been described using a set of numerical upper limits and a set of numerical lower limits. When numerical lower limits and numerical upper limits are listed herein, ranges from any lower limit to any upper limit are contemplated, and are expressly within the scope of the invention. Certain lower limits, upper limits and ranges appear in one or more claims below. All numerical values take into account experimental error and variations that would be expected by a person having ordinary skill in the art. The term "comprising" is synonymous with the term "including". Likewise whenever a composition, an element or a group of components is preceded with the transitional phrase "comprising", it is understood that we also contemplate the same composition or group of components with transitional phrases "consisting essentially of," "consisting of", "selected from the group consisting of," or "is" preceding the recitation of the composition, component, or components, and vice versa.

Various terms have been defined above. To the extent a term used in a claim is not defined above, it should be given the broadest definition persons in the pertinent art have given that term as reflected in at least one printed publication or issued patent. Furthermore, all patents, patent applications, any test procedures, and other documents cited in this application are fully incorporated by reference in their entirety to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The invention claimed is:

1. A process for producing aromatic hydrocarbon comprising the steps of:
   (a) providing a feedstock comprising a non-aromatic hydrocarbon to a reaction zone;
   (b) providing a catalyst to the reaction zone, wherein (i) the catalyst has catalytic activity to form aromatic hydrocarbon from the non-aromatic hydrocarbon, (ii) the catalyst comprises at least one molecular sieve component and at least one dehydrogenation component, the catalyst is a self-bound catalyst comprising ≤5 wt. % of a binder, based on the weight of the catalyst, and the catalyst is produced by a process comprising (1) mulling the molecular sieve with water to a solids level of 25 to 75 weight percent in the presence of 0.25 to 10 weight percent of a base, calculated as solid base, based on total solids content, and (2) extruding the mulled mixture to obtain an extrudate, (iii) the molecular sieve component is present in the catalyst in an amount ≥90 wt. % based on the weight of the catalyst, and (iv) the dehydrogenation component comprises either one or two metal elements, the one or two metal elements are Zn or a combination of Zn and Ga, and the dehydrogenation component is impregnated on the molecular sieve component; and
   (c) converting ≥1 wt. % of the non-aromatic hydrocarbon in the feedstock to produce a product comprising ≥1 wt. % of the aromatic hydrocarbon, the conversion being carried out in the presence of the catalyst under conversion conditions which include a temperature ≥400° C.

2. The process of claim 1, wherein the process exhibits a reduction in aromatic hydrocarbon yield that does not exceed 10% when the catalyst achieves a time-on-stream in conversion mode of 20 hours from the start of the conversion, and the conversion conditions further include a temperature in a range of about 450° C. to 750° C., a pressure in a range of from about 35 kPa to about 1480 kPa, and a weight hourly space velocity (WHSV) in a range of from 0.1 $hr^{-1}$ to 20 $hr^{-1}$.

3. The process of claim 2, wherein the reduction in aromatic hydrocarbon yield does not exceed 10% when the catalyst achieves a time-on-stream in conversion mode of 50 hours from the start of the conversion.

4. The process of claim 1, wherein the aromatic hydrocarbon comprises single ring aromatic hydrocarbon, multiple-ring aromatic hydrocarbon, or mixtures thereof.

5. The process of claim 4, wherein (i) the feedstock is natural gas and (ii) the single-ring aromatic hydrocarbon is selected from the group consisting of benzene, toluene, xylenes, and mixtures thereof.

6. The process of claim 4, wherein the multiple-ring aromatic hydrocarbon is naphthalene.

7. The process of claim 1, wherein the catalyst is located in at least one fixed catalyst bed in the reaction zone.

8. The process of claim 1, wherein the molecular sieve component comprises a crystalline aluminosilicate having a constraint index in the range of 1 to 12.

9. The process of claim 8, wherein the crystalline aluminosilicate is one or more of MCM-22 crystalline aluminosilicate, ZSM-5, ZSM-11, ZSM-12, ZSM-21, ZSM-22, ZSM-23, ZSM-35, ZSM-38, ZSM-48, ZSM-50, ZSM-57, MCM-68, and mixtures thereof.

10. The process of claim 1, wherein (i) the feedstock comprises at least 10 wt. % $C_2$ to $C_5$ non-aromatic hydrocarbon, by weight of the feedstock, and (ii) the dehydrogenation component comprises ≥90 wt. % of Ga or Zn or a mixture thereof, based on the weight of the dehydrogenation component.

11. The process of claim 10, wherein the catalyst includes Zn or a combination of Zn and Ga in an amount in the range of 0.005 wt. % to 5 wt. %, based on the weight of the catalyst.

12. The process of claim 10, wherein:
(i) the molecular sieve component comprises ≥90 wt. % of at least one molecular sieve,
(ii) the molecular sieve has a framework of interconnected atoms,
(iii) the molecular sieve has an outer surface and a plurality of pores having an average pore size of 4 Å to 7 Å,
(iv) ≥90 wt. % of the one or two metal elements of the dehydrogenation component is located in the pores, and ≤10 wt. % of the one or two metal elements is proximate to the outer surface, and
(v) the catalyst includes ≤10 wt. % of metal in any form other than framework metal if any.

13. The process of claim 12, wherein:
(i) the catalyst includes the molecular sieve in an amount ≥95 wt. % based on the weight of the catalyst,
(ii) the molecular sieve comprises ≥90 wt. % of one or more of MCM-22, ZSM-5, ZSM-11, ZSM-12, ZSM-22, ZSM-23, ZSM-35, and ZSM-48, and (iii) the catalyst includes the one or two metal elements of the dehydrogenation component in an amount ≥0.005 wt. % based on the weight of the catalyst.

14. The process of claim 13, wherein ≥90 wt. % of molecular sieve is ZSM-5.

15. The process of claim 1, wherein the catalyst includes the molecular sieve component in an amount ≥95 wt. % of the catalyst.

16. The process of claim 1, wherein the catalyst includes ≤1 wt. % of binder.

17. The process of claim 13, wherein ≥90 wt. % of molecular sieve is ZSM-5, the catalyst further comprises element P, and Zn constitutes 50-70 wt % of the total weight of Zn and element P, and element P constitutes 30-50 wt % of the total weight of Zn and element P.

18. The process of claim 1, in which the process exhibits no more than a 10% reduction in yield of aromatic hydrocarbon after use of the catalyst for greater than 50 hours of time on stream.

19. The process of claim 12, in which the process exhibits no more than a 10% reduction in yield of aromatic hydrocarbon after use of the catalyst for greater than 50 hours of time on stream.

20. The process of claim 13, in which the process exhibits no more than a 10% reduction in yield of aromatic hydrocarbon after use of the catalyst for greater than 50 hours of time on stream.

21. The process of claim 1, in which the catalyst has an alpha value of less than 460 before metal is added.

22. The process of claim 12, in which the catalyst has an alpha value of less than 460 before metal is added.

23. The process of claim 13, in which the catalyst has an alpha value of less than 460 before metal is added.

24. A process for producing aromatic hydrocarbon comprising the steps of:
(a) providing a feedstock comprising 10 wt. % of $C_2$-$C_5$ non-aromatic hydrocarbon, based on the weight of the feedstock, and a methane diluent to a reaction zone;
(b) providing a catalyst to the reaction zone, wherein (i) the catalyst has catalytic activity to form aromatic hydrocarbon from the non-aromatic hydrocarbon, (ii) the catalyst comprises at least one molecular sieve component and at least one dehydrogenation component comprising either one or two metal elements, the one or two elements being Zn or a mixture of Zn and Ga, the at least one dehydrogenation component being impregnated on the molecular sieve component, the catalyst is a self-bound catalyst comprising ≤5 wt % of a binder, based on the weight of the catalyst, and the catalyst is produced by a process comprising (1) mulling the molecular sieve with water to a solids level of 25 to 75 weight percent in the presence of 0.25 to 10 weight percent of a base, calculated as solid base, based on total solids content, and (2) extruding the mulled mixture to obtain an extrudate, and (iii) the molecular sieve component is present in the catalyst in an amount ≥90 wt. % based on the weight of the catalyst; and
(c) converting ≥1 wt. % of the non-aromatic hydrocarbon in the feedstock to produce a product comprising ≥1 wt. % of the aromatic hydrocarbon, the conversion being carried out in the presence of the catalyst under conversion conditions that include a temperature in the range 450-605° C.

25. The process of claim 24, wherein the catalyst further comprises the element P.

26. The process of claim 25, in which the molecular sieve component is present in the catalyst in an amount ≥95 wt. % based on the weight of the catalyst.

27. The process of claim 24, wherein:
(i) the molecular sieve has a framework of interconnected atoms,
(ii) the molecular sieve has an outer surface and a plurality of pores having an average pore size of 4 Å to 7 Å,
(iii) ≥90 wt. % of the one or two metal elements of the dehydrogenation component is located in the pores, and ≤10 wt. % of the one or two metal elements is proximate to the outer surface, and
(iv) the catalyst includes ≤10 wt. % of metal in any form other than framework metal if any.

28. The process of claim 27, wherein:
(v) the catalyst includes the molecular sieve in an amount ≥95 wt. % based on the weight of the catalyst,
(vi) the molecular sieve comprises ≥90 wt. % of one or more of MCM-22, ZSM-5, ZSM-11, ZSM-12, ZSM-22, ZSM-23, ZSM-35, and ZSM-48, and
(vii) the catalyst includes the one or two metal elements of the dehydrogenation component in an amount ≥0.005 wt. % based on the weight of the catalyst.

29. The process of claim 24, in which the process exhibits no more than a 10% reduction in yield of aromatic hydrocarbon after use of the catalyst for greater than 50 hours of time on stream.

30. The process of claim 24, in which the catalyst has an alpha value of less than 460 before metal is added.

* * * * *